United States Patent [19]

Schultz et al.

[11] Patent Number: 4,904,274
[45] Date of Patent: Feb. 27, 1990

[54] COLORING HAIR WITH AMINOALKYL-OR AMINOHYDROXYALKYL-CATECHOLS

[75] Inventors: Thomas M. Schultz, Highland Mills, N.Y.; Leszek J. Wolfram, Stamford; Keith C. Brown, New Canaan, both of Conn.; Giuseppe Prota, Naples, Italy

[73] Assignee: Clairol Incorporated, Stamford, Conn.

[21] Appl. No.: 193,694

[22] Filed: May 12, 1988

[51] Int. Cl.$^4$ ................................................. A61K 7/13
[52] U.S. Cl. ............................................ 8/406; 8/429; 8/623; 8/624; 8/629
[58] Field of Search .................. 8/406, 623, 624, 408, 8/410, 412, 414, 416, 421, 429, 629

[56] References Cited

FOREIGN PATENT DOCUMENTS 146977 6/1978 Japan.
3072836 6/1978 Japan.

*Primary Examiner*—Paul Lieberman
*Assistant Examiner*—John F. McNally
*Attorney, Agent, or Firm*—Sandra M. Nolan

[57] ABSTRACT

A process for coloring hair in which a functional metal ion and aminoalkyl or aminohydroxyalkyl catechols are used in combination or applied sequentially to dye the hair rapidly.

16 Claims, No Drawings

COLORING HAIR WITH AMINOALKYL- OR AMINOHYDROXYALKYL-CATECHOLS

This invention relates to an improved process for dyeing hair on the human scalp or head that utilizes certain aminoalkyl or aminohydroxy alkyl catechols as the essentially sole chromogenic agent with or without color modifiers such as phenylenediamines, nitrobenzenes or similarly used direct dyeing agents common in the art of coloring the hair. More particularly, the invention relates to the use of certain metal ions as catalytic agents for an efficient in situ conversion of said chromogenic agent to melanin-like, durable dyes, whereby certain deficiencies in the procedures previously reported are markedly reduced.

The aminoalkyl- or aminohydroxyalkyl catechols that are useful for the purposes of this invention are more particularly described by the formula.

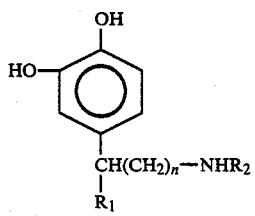

wherein
(1) $R_1$ is H or OH;
(2) $R_2$ is H or alkyl; and
(3) n is 0 or 1.

When $R_2$ is alkyl, it is preferably, a lower alkyl radical having from 1 to about 4 or 6 carbon atoms.

Some literature exists on the possible use of aminoalkyl catechols, particularly dopa, as coloring agents for the hair. Typically, an alkaline solution of DOPA is applied to the hair and after 45 to 90 minutes, a dark brown or black (color) is obtained. The characteristics claimed for such treatments are a natural feel and permanent coloring. There are, however, deficiencies in the practical use of this procedure in that alkaline solutions of aminoalkyl catechols are very unstable, requiring them to be prepared freshly before use. Additionally, the dyeout time is too long and severe staining of the skin occurs.

THE INVENTION

It has now been found that if the hair is treated with a metal salt supplying functional metal ions, satisfactory dyeouts with hair dye compositions containing a compound of formula I above can be obtained in a much shorter period of time than that obtained with the prior art processes. Furthermore, it has been found that this treatment can be accomplished at ambient temperatures (e.g. 20°-35°) which can be readily tolerated by the human scalp and does not require the use of $H_2O_2$ as is characteristic of somewhat related processes. In addition, a variety of color hues can be obtained ranging from black to medium or golden brown by suitable modifications in the hair dye composition. Although the precise mechanism of color formation is not known, there is reason to believe that in the presence of metal ions both the binding of the aminoalkyl- or aminohydroxyalkyl catechols to the hair and its subsequent conversion to melanin like durable dyes are favored, thereby the dyeing process is significantly improved.

PRIOR ART

A procedure which has been suggested in the prior art for hair dyeing involves the use of an aminoalkyl catechol in a non-alkaline solution containing an oxidizing system. This is exemplified by European Pat. No. 161073A of 1984 which claims a process of dyeing hair with, e.g., dopamine in a combination containing iodate and a persulfate or periodate. It is said to dye hair pleasing shades of brown and black. However, this requires a treatment that takes over 60 minutes.

Soviet Union Pat. No. 566,895 (Fu.Prod.Res.Inst., 1985) describes the use of epinephrine to dye furs dark brown to black. According to this procedure, furs, as distinguished from human hair on the head, are first treated with a metal salt at 1% to 3% weight/weight or a mixture of metal salts for 3 to 6 hours. This is followed by soaking the treated furs from 3 to 6 hours in a bath containing 20% $H_2O_2$ and epinephrine. It is obviously prohibitive to dye human hair on the head using such treatment conditions. Moreover, this patent teaches that $H_2O_2$ must be used as a second step and it is implied that the coloring process itself would be inoperative without the second step.

It was surprising to discover that application of compound I to metal-ion pretreated hair gave a natural looking dyeout in a very short time. In addition, no harsh oxidizing agents such as hydrogen peroxide are required as has been taught in the prior art.

U.S. Pat. No. 4,453,941 to Jacobs relates to a process for producing pigmentation in hair or on skin. This process involves treating hair with a reaction product of, for example, N-acetyldopamine and an omega amino acid. In column 3 beginning at 47, the patentee describes a process wherein lengths of gray human hair were soaked with a 0.1M copper chloride solution. The hair is then rinsed and soaked at 25° C. with a mixture of 0.01M N-acetyldopamine and 0.1M beta-alanine. The hair is said to assume a golden blond color. This disclosure is different from the present invention in several significant respects. In the first place, the N-acetyldopamine employed is not a compound that falls within the definition of the formula I compounds that are useful for the purposes of the present invention.

Indeed, N-acetyldopamines are known to undergo indolization reactions very poorly which limits their ability to give melanin-like materials. As a result, under most dyeing conditions, they produce only low intensity dyeouts of light shades.

Moreover, the Jacobs patent requires, as a matter of necessity, the inclusion of an amino acid such as beta-alanine in the treatment composition. As a matter of fact, Jacobs goes to great pains to point out that his coloring agent is a reaction product of the N-acetyldopamine and the beta-alanine. This is clearly quite different from the case of the present invention wherein there is no necessity that the compound I components be reacted with a second compound to generate the color producing agent.

Japanese Pat. No. 50130443 teaches a three step process for coloring hair involving:

(a) contacting the hair with a bisulfite solution;
(b) treating the hair with a solution containing $Cu^{+2}$ or $Fe^{+2}$ ions; and
(c) applying a combination of dopamine and a polyhydroxybenzene.

Much as in the case with the Jacobs patent, this process relies on the combination of complex reaction products, e.g. dopamine and a polyhydroxy benzene. This is clearly quite different from the present invention, which involves using a compound I material as the color forming agent.

DESCRIPTION OF INVENTION

The process of the present invention in its broader aspects visualizes that the metal ion and the formula I compound may be applied to the hair either concurrently or sequentially. However, in the preferred mode of practicing the process of this invention these will be applied sequentially, the metal ion being applied to the hair first.

To simplify the description of this invention, emphasis will be placed hereinafter on the preferred sequential treatment process. As will be described in more detail below, this sequential treatment also includes the case wherein the metal ion pre-treated hair is dyed with a composition containing both the formula I compound and another metal ion (e.g., those demonstrated in Examples 13, 15, 16 and 18).

As indicated previously, any compound falling within formula I above would be useful in the practice of the present invention. By way of more specific exemplification of such compounds, the following may be mentioned: 3,4-dihydroxyphenylethylamine (Dopamine); epinephrine; 3,4-dihydroxybenzylamine; 2-hydroxy-2-(3,4-dihydroxyphenyl)ethylamine, i.e.

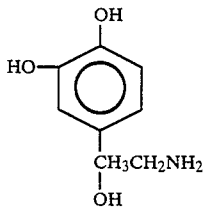

The formula I compound will usually be applied to the hair from a hair dye composition containing the same. This hair dye composition will ordinarily take the form of an aqueous composition containing the formula I compound in a concentration sufficient to impart the desired color to the metal ion treated hair. Generally, it will be present in said hair dye composition at a concentration in the range of from about 0.1% to about 5% by weight based on the total weight of said composition with the preferred range being from about 1% to about 2% on the same weight basis.

One of the advantages of the present invention is that the formula I compound may be applied to hair over a wide range of pH, e.g. from about 4 to 10. However, exceptionally good results are obtained with a pH range of about 5 to about 9, with the preferred range being from about 5 to about 7.

It has been found to be advantageous, although not necessary, to also include an oxidant in the composition used in coloring the metal ion treated hair. When this is the case, an oxidant composition is prepared which will be mixed with the hair dye composition containing the aminoalkyl- or aminohydroxyalkyl-catechols just before use to form a hair dye composition now containing the oxidant as well as the catecholamine. Any of a variety of oxidants may be employed for the purposes of the present invention. By way of example, mention may be made of the following: hydrogen peroxide, persulfate (Na or K salt), percarbonates (Ba, Na, or K salts), periodate (Na or K salts), etc.

However, optimum results are obtained when the oxidant is selected from the group consisting of a peroxide (e.g. $H_2O_2$, benzoyl peroxide, or urea peroxide), an iodate (i.e. $IO_3$), a persulfate, a periodate or combinations thereof. The persulfate or the periodate will usually take the form of their respective alkali metal (e.g. Na, K, Li) or alkaline earth metal (e.g. Ca, Ba, Ti) salts.

The oxidant serves to accelerate even further the rate of the color formation beyond the rapid increase already caused by treating the hair with a metal-ion.

The concentration of the oxidant contained in the hair dye composition (i.e. the composition formed by mixing the catecholamine composition with the oxidant system) may vary somewhat. Generally the oxidant will be present in said composition at a concentration in the range of from about 0.05% to about 3% by weight based in the total weight of of the hair dye composition with the preferred range being from about 1% to about 2% on the same weight basis.

The hair dye composition used in the practice of this invention, aside from the formula I compounds may also contain a variety of adjuvants commonly used in the hair dye art to facilitate the dyeing of the hair or that will improve the organoleptic qualities of the composition. For example, dye penetration enhancers, such as phenoxyethanol, benzyl alcohol, isopropanol and others, can be successfully employed.

As used herein the term "hair dye composition" refers both to the simple formula I compound compositions and to the simple formula I compound compositions to which have been added the oxidant compositions. Accordingly, the final composition employed in practicing the process of this invention may also contain the adjuvants present in the simple aminoalkyl- or aminohydroxyalkyl-catechol composition or the adjuvants contained in both the simple aminoalkyl- or aminohydroxyalkyl-catechol composition and in the oxidant system.

As indicated above it is a feature of the present invention to contact the hair on the head of a subject with at least one metal salt that provides functioning metal ions prior to subjecting said hair to the hair dyeing operation with a composition containing a formula I compound. As used herein the term "functioning metal ions" means any metal ion which accelerates the formation of melanin-like materials from the aminoalkyl- or aminohydroxyalkyl catechols. Salts of any of a variety of metals, which are preferably water soluble, may be employed for this purpose. By way of example of the metallic moieties of the salts that may be used in accordance with the present process the following may be mentioned: copper (e.g. $Cu^{+2}$), titanium (e.g. $Ti^{+2}$), zinc (e.g. $Zn^{+2}$), iron (e.g. $Fe^{+2}$ and $Fe^{+3}$) nickel (e.g. $Ni^{+2}$), cobalt (e.g. $Co^{+2}$), lead (e.g. $Pb^{+2}$), silver (e.g. $Ag^{+1}$) and manganese (e.g. $Mn^{+2}$). All of these metal ions given by way of illustration are capable of assisting the conversion of formula I compounds to melanin-like materials. However, this list is not exhaustive of the metal salts that can be employed herein and is not intended to exclude or limit the scope of such metal ions that are useful in this hair coloring process.

The anionic moieties of these salts may be exemplified by such anions as sulfate, lactate, tartrate, acetate, citrate, nitrate and chloride. Again, this listing is not exhaustive of those anions of the metal salts employable in this invention. By way of illustration of specific salts which may be used in the pre-treatment of hair according to the present invention the following salts may be mentioned $CuSO_4$, $Ti(lactate)_2$, $Fe(NO_2)_3$, $FeSO_4$, $K_3Fe(CN)_6$, $Pb(acetate)_2$, $Cu(II)$ $(Citrate)$, $ZnSO_4$, $NiSO_4$, $Co(acetate)_2$, $Ag(Nitrate)$, $Mn(nitrate)_2$, $Mn(Cl)_2$, etc.

The salts used in accordance with the present invention will ordinarily be applied to the hair from a composition containing the same which will usually be an aqueous composition. The concentration of the metal salt contained in this composition will vary somewhat, but generally will fall into the range of from about 0.001% to about 2% by weight based on the total weight of the metal salt composition, with the preferred range being from about 0.01% to about 1% on the same weight basis. A convenient way of applying the metal salt is from a shampoo composition. In this event the metal salt composition in addition to detergents will also contain the adjuvants found in shampoo compositions. These include such items as amides, fatty acids, cocamidopropyl betaine, fragrance, preservatives, etc.

In carrying out the process of the present invention the hair on the human head is contacted with a metal salt containing composition as described above. Typically the metal salt concentration will be in the range from about 0.001% to about 5%. This composition is allowed to remain in contact with the hair for a period of from about 1 minute to about 45 minutes; preferably from about 5 minutes to about 15 minutes. The hair can then be shampooed. This process will ordinarily be carried out at room temperatures although elevated temperatures may be employed, such as those which can be achieved with commercial hair dryers.

Following the treatment with the aforesaid metal salts the hair is contacted with a solution of the formula I compound (e.g. 0.05% to 2% solution). The pH of this composition may vary but typically it will be in the range of from about 5 to about 7. The length or duration of application may vary somewhat depending on the results desired. Usually, however, this will be in the range of from about 5 to about 15 to 30 minutes.

Dyeing may be accomplished at any of a variety of temperatures. Preferably temperatures will be close to room temperatures (e.g. from about 20° C. to 35° C.). However, under some circumstances it may be advantageous to carry out this procedure at an elevated temperature, for example that achieved with commercial hair dryers.

In some cases, it may be desirable to mix the metal salt with a formula I compound and use this mixture to treat hair that has been previously treated with a metal salt. Thus, for example, an $Fe^{++}$ salt may be mixed with epinephrine to form a solution having a pH from about 5 to 7. This composition may be used to dye hair that has been previously treated with a $Cu^{++}$ or $Fe^{+3}$ salt. Treatment of the latter kind for a period of 20 to 30 minutes gives a medium golden brown dyeout.

The significant advantage to this method is the lack of any added oxidant or potential oxidant such as $IO_3$, persulfate, or the like. Thus, whereas it is desirable to use an oxidant in the presence of a metal-salt already applied to the hair, in certain instances the aminoalkyl- or aminohydroxyalkyl-catechols conversion to a melanin does not require such oxidant and the combination of metal-salts suffice.

Alternatively the formula I compound solution may be mixed, for example, with 0.1 to 3% of an oxidant such as peroxide (e.g. hydrogen peroxide, benzoyl peroxide, or urea peroxide), persulfate (as the sodium or potassium salt), or a perhalite (e.g. periodate, perchlorate, or perborate) immediately prior to application to hair previously treated with a metal salt. This gives a light medium brown dyeout typically in less than 20 minutes. As in the other procedure, the dyeout is preferably performed at room temperatures (i.e. 20° C. to 35° C.). Although in some cases this may be done at elevated temperatures as, for example, that achieved with a commercial hair dryer.

When the hair dye composition employed contains both an aminoalkyl- or aminohydroxyalkyl-catechol and an oxidant this will generally be prepared first prior to the application to the hair. In this case a dye concentrate containing an aminoalkyl- or aminohydroxyalkyl-catechol will be mixed with an oxidizing composition containing one or more oxidants to obtain the hair colorant formulation. The dye concentrate employed will contain an aminoalkyl- or aminohydroxyalkyl-catechol in the concentration range of from about 0.1% to about 5% by weight based on the total weight of the dye concentrate with the preferred concentration following in the range of from about 1% to about 2% on the same bases. The oxidizing composition, on the other hand, will contain the oxidant component or components in a concentration in the range of from about 1% to about 6% by weight based on the total weight. In this case the preferred concentration range is from about 1% to about 2% by weight based on the total weight of the oxidizing composition. To prepare the hair colorant formulation, i.e., the composition containing both an aminoalkyl- or aminohydroxyalkyl catechol and one or more oxidants, from about 0.5 to about 2 parts by weight of the oxidizing composition per part of dye concentrate will be mixed with each other just prior to use.

The colors obtained on hair from the exposure of metal salt pre-treated hair to an aminoalkyl- or aminohydroxyalkyl-catechol composition with or without an oxidant range from light to brown to black. It is sometimes advantageous to lighten the dark dyeouts to a golden brown or a dark brown. This may be accomplished, in accordance with the present invention, by a post-treatment of the hair dyed as described above with an oxidizing agent, such as an aqueous $H_2O_2$ solution in which the concentration of the $H_2O_2$ in said solution is in the range of about 0.1% to about 6% by weight based on the total weight of the aqueous composition and having an alkaline pH (e.g., pH 9 has been found to be quite suitable). The hair is quickly lightened by saturating said aminoalkyl- or aminohydroxyalkyl-catechols dyed metal salt treated hair with this oxidizing solution for about 5 minutes to about 10 minutes and then rinsing the hair.

The following example sets forth a general procedure for dyeing hair with a process of metal-salt embrocation and the sequential treatment with aminoalkyl- or aminohydroxyalkyl-catechols. Following this example is Table I which details various metal-salt, aminoalkyl- or aminohydroxyalkyl-catechols and buffer solutions found to be useful. Next listed is Table II which further exemplifies the breadth of dyeout colors achievable. It is understood, however, that this invention is not limited thereto.

GENERAL EXAMPLE OF HAIR DYEING.

Solution A is made up by dissolving 2% dopamine (wt/wt) (i.e. 3,4-dihydroxyphenyethylamine) at pH 7 in buffered water containing 1% (wt/wt) of iodate ($IO_3$, either the sodium or potassium salt). Next a metal-salt solution is made by dissolving 0.04M copper sulfate in a solution of 1% monoethanolamine (vol/vol) in water and then treating blended grey hair in this solution for 5 minutes. The hair is then rinsed with water and patted dry. Next the hair swatch is treated for 15 minute in solution A for 15 minutes to give a of dark brown dyeout with yellow hues. The prior art which does not use a metal ion requires 45 to 90 minutes to obtain dark grey to black dyeouts.

Other useful compositions are set out in Table I. These compositions were used in procedures which were substantially similar to that described above, except that the reagents and other parameters used were those listed in the table.

Table II sets forth another set of reagents. The metal-salt solutions were applied for about five minutes. The catecholamines were applied for about 10 minutes. The resultant colors are given in the tables.

TABLE I

A Compilaton of Buffer, Metal-salt and Substitued Catechol Solution Preparations and Compositions

| | Solution | Metal Salt gm/100 ml | Buffer Components wt % | Catecholamine wt/1% (gms/100 ml) | Oxidant wt/% | QS Water | pH |
|---|---|---|---|---|---|---|---|
| 1. | Dopamine | | 0.1 gm $NaH_2PO_4$/0.2 gm $Na_2HPO_4$ | 1.0 gm Dopamine | | 100 | 7 |
| 2. | Dopamine + $IO_3$ | | 0.1 gm $NaH_2PO_4$/0.2 gm $Na_2HPO_4$ | 2.0 gm Dopamine | 1.0 gm $NaIO_3$ | 100 | 7 |
| 3. | Norepinephrine + persulfate | | 0.1 gm $NaH_2PO_4$/0.2 gm $Na_2HPO_4$ | 2.0 gm Norepinephrine | 1.0 gm $Na_2S_2O_8$ | 100 | 7 |
| 4. | Dopamine + persulfate | | 0.1 gm $NaH_2PO_4$/0.2 gm $Na_2HPO_4$ | 2.0 gm Dopamine | 1.0 gm $Na_2S_2O_8$ | 100 | 7 |
| 5. | Epinephrine + $Fe(SO_4)_2$ | 1.0 gm $(NH_4)_2Fe(SO_4)_2.6H_2O$ | 0.1 gm $H_3PO_4$ + 0.3 gm $NH_2CH_2CH_2CH$ | 1.0 gm Epinephrine | — | 100 | 6 |
| 6. | Epinephrine + $Fe(CN)_6^{-3}$ | 1.0 gm $K_3Fe(CN)_6$ | 0.1 gm $H_3PO_4$+ 0.2 g $NaCOOCH_3$ | 1.0 gm Epinephrine | — | 100 | 5 |
| 7. | Dopamine + Ferric Nitrate | 1.0 gm Na $Fe(NO_3)_3$ | 0.1 gm HCl + 1.0 gm $NH_2CH_2CH_2OH$ | 1.0 gm Dopamine | — | 100 | 7 |
| 8. | Dopamine + $Fe(SO_4)_2$ | 1.0 gm $(NH_4)_2 Fe(SO_4)_2.6H_2O$ | 0.1 gm $H_3PO_4$ + 0.3 gm $NH_2CH_2CH_2OH$ | 1.0 gm Dopamine | — | 100 | 6 |
| 9. | 3,4 dihydroxy-benzylamine | | 0.1 gm $H_3PO_4$ | 1.0 gm 3,4-dihydroxy-benzylamine | | 100 | 5 |
| 10. | 3,4-dihydroxy-benzylamine + $IO_3$ | | 1.0 gm $H_3PO_4$ | 1.0 gm 3,4-dihydroxy-benzylamine | 1.0 g $NaIO_3$ | 100 | 5 |
| 11. | 3,4-dihydroxy-benzylamine + $Fe(SO_4)_2$ | 1.0 gm $(NH_4)_2 Fe.(SO_4)_2. 6H_2O$ | 0.1 gm $H_3PO_4$ + 0.3 gm $NH_2CH_2CH_2OH$ | 1.0 gm 3,4-dihydroxy-benzylamine | | 100 | 5 |
| 12. | $CUSO_4$ | 1.0 gm $CUSO_4.5H_2O$ | 2.0 gm $NH_2CH_2CH_2OH$ | | | 100 | 9 |
| 13 | Zn(OAc) | 1.0 gm $Zn(OAc)_2$ | 1.0 gm $H_3PO_4$ | | | 100 | 4 |
| 14. | Ti(Lactate) | 1.0 g $Ti(CH_3COH—CO_2O)_2$ | 1.0 gm $HOCOCH_3$ + 0.5 gm $NaCO_2CH_3$ | | | 100 | 5 |
| | | | | | | 100 | 5 |
| 15. | $Fe(SO_4)_2$ | 1.0 gm $(NH_2)_2 Fe.(SO_4)_2. 6H_2O$ | 0.1 gm $H_3PO_4$ + 0.3 gm $NH_2CH_2CH_2OH$ | | | 100 | 5 |

TABLE II

Examples of dyeing Natural Blended Grey Hair by the Sequential Application of a Metal-salt Solution (Listed horizontally) Followed by the Catecholamine (Listed Vertically) for 10 Minutes

| Catecholamine | None | 1% CuSO$_4$ | 1% CuSO$_4$ + 1% IO$_3$ | 1% Zn(OAc)$_2$ | 1% Ti(lactate)$_2$ | 1% Fe(CN)$_6$ | 1% Fe(SO$_4$) |
|---|---|---|---|---|---|---|---|
| 1% Dopamine pH 7 | Ex. 1 Light Ash Brown | | | | | | |
| 2% Dopamine + 1% IO$_3$ pH 7 | | Ex. 2 Dark Brown with yellow hues | | Ex. 3 Dark Brown with Blue highlights | Ex. 4 Medium Golden Brown with Light Yellow Hues | | |
| 2% Norepinephrine + 1% persulfate pH 7 | Ex. 5 Medium Golden Brown | Ex. 6 Golden Brown | | | | | |
| 2% Dopamine + 1% persulfate pH 7 | | | | | Ex. 9 Light Golden brown | | |
| 1% Epinephrine + 1% FeSO$_4$ (II) pH 6 | | Ex. 10 Medium Golden Brown | | | | Ex. 11 Medium Brown | |
| 1% Epinephrine + 1% Fe(CN)$_6$ pH 5 | | | Ex. 13 Light Ash Brown | | | | Ex. 12 Very Light Golden Brown |
| 1% Dopamine + 1% Ferric Nitrate pH 7 | | | Ex. 14 Medium Ash Brown | | | | |
| 1% Dopamine + 1% Fe$^{+2}$ SO$_4$ pH 6 | | Ex. 15 Golden Brown | | | | | |
| 1% 3,4-dihydroxy-benzylamine pH 7 | | Ex. 16 Medium Brown | 1% IO$_3$ | | Golden | | |
| 1% 3,4-dihydroxy-benzylamine + pH 6 | | Ex. 17 Dark Charcoal Grey | | | | | |
| 1% 3,4-dihydroxy-benzylamine + 1% Fe$^{+2}$ SO$_4$ pH 6 | | | | | | | |

TABLE III

The Hair Dyed as per Examples in Table II
Was Lightened By Treating the Dyed Swatches with 3% $H_2O_2$
At pH 9 (monoethanolamine buffered) For 5 Minutes.
All Tresses were Originally Composed of Natural Blended Grey Hair
The Results Are Given in Table III

| Metal-Ion/Substituted Catechol Combination; pH | Dyeout Color Before Bleaching | Dyeout Color After Bleaching |
|---|---|---|
| Ex. 18 $Cu^{+2}$ pretreatment/ 1% Dopamine + 1% $IO_3$ at pH 7 | Dark Brown with Yellow Hues | Light Golden Brown |
| Ex. 19 $Ti^{+2}$ pretreatment/ 1% Dopamine + 1% $IO_3$ at pH 7 | Medium Golden Brown Highlights | Light Golden Brown |
| Ex. 20 $Zn^{+2}$ pretreatment/ 1% Dopamine + 1% $IO_3$ at pH 7 | Dark Brown with Blue Highlights | Light Golden Brown |
| Ex. 21 $Fe(CN)_6^{-3}$ pretreatment/1% Epinephrine + 1% $Fe^{+2}$ at pH 6 | Medium Brown | Straw Colored |
| Ex. 22 $Fe^{+2}$ pretreatment/ 1% Epinephrine + 1% $Fe(CN)_6^{-3}$ at pH 6 | Dark Golden Brown | Lustrous Golden Brown |

Reasonable variations, such as those which would occur to a skilled artisan, can be made herein without departing from the scope of the invention.

What is claimed is:

1. A process for coloring hair which comprises treating said hair with a metal salt capable of assisting the conversion of a catechol compound to a melanin-like material and an aminoalkyl- or aminohydroxyalkyl-catechol having the formula:

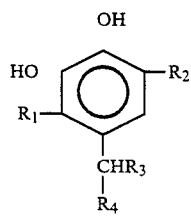

wherein:
(a) $R_1$ and $R_2$ are radicals selected from the group consisting of H, OH, alkyl, alkoxy, alkoxyalkyl, $NO_2$, —COOH and carboalkoxy;
(b) $R_3$ is selected from the group consisting of $R_1$ and $NH_2$;
(c) $R_4$ is selected from the group consisting of H, —$CH_2NHR_5$, —$CHOHNHR_5$, —CH(alkyl)$NHR_5$, —CH($NHR_2$) $NHR_5$, CH($NO_2$)$NHR_5$, —CH(alkoxy)$NHR_5$, CH($NHR_2$)$NHR_5$, —CH(alkoxy)$NHR_5$ —CH(carboxy)$NHR_5$, —CH(carboalkoxy)$NHR_5$), —CH(aryl)$NHR_5$ —CH(aryloxy)$NHR_5$, or —CH(halogen)$NHR_5$; wherein $R_5$ is selected from H, alkyl or aryl, and wherein
(d) at least one of $R_1$, $R_2$, $R_3$ or $R_4$ is an amino group bonded to a ring carbon atom of said formula through an alkylene bridging group.

2. The process according to claim 1 wherein said metal salt and said aminoalkyl- or aminohydroxyalkyl-catechol are applied concurrently.

3. The process according to claim 1 wherein said metal salt and said aminoalkyl- or aminohydroxyalkyl-catechol are applied sequentially.

4. The process according to claim 3 in which said metal salt is first applied to the hair to form a metal ion deposit on the hair which is followed by an application of the aminoalkyl- or aminohydroxyalkyl-catechol.

5. The process according to claim 4 wherein said composition containing said aminoalkyl- or aminohydroxyalkyl-catechol also contains a metal salt.

6. The process according to claim 4 wherein said composition containing said aminoalkyl- or aminohydroxyalkyl-catechol also contains an oxidant.

7. The process according to claim 6 wherein said oxidant is selected from the group consisting of a peroxide, an iodate, a persulfate, a periodate and combination thereof.

8. The process according to claim 4 including the step of post-treating hair colored in accordance therewith with an aqueous composition of hydrogen peroxide for sufficient time to lighten the color.

9. The process according to claim 7 including the step of post-treating hair colored in accordance therewith with an aqueous composition of hydrogen peroxide for sufficient time to lighten the color.

10. The process according to claim 4 wherein said aminoalkyl- or aminohydroxyalkyl-catechol is of the formula:

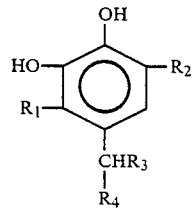

wherein:
(a) $R_1$ and $R_2$ are radicals selected from the group consisting of H, OH, alkyl, alkoxy, alkoxyalkyl, $NO_2$, COOH and carbalkoxy;
(b) $R^3$ is selected from the group consisting of $R_1$ and $NH_2$;

(c) R₄ is selected from the group consisting of H,—CH₂NHR₅, —CHOHNHR₅, —CH(alkyl)NHR₅, —CH(NHR₂)NHR₅, —CH(NO₂)NHR₅, —CH(alkoxy)NHR₅, —CH(NHR₂)NHR₅, —CH(NO₂)NHR₅, —CH(alkoxy)NHR₅ —CH(carboxy) NHR₅, —CH(carboalkoxy)NHR₅), —CH(aryl)NHR₅ —CH(aryloxy)NHR₅, or —CH(halogen)NHR₅; wherein R₅ is selected from H, alkyl or aryl, and wherein (d) at least one of R₁, R₂, R₃ or R₄ amino group bonded to a ring carbon atom of formula I through an alkylene bridging group.

11. A process according to claim 4 wherein said metal salt is present in said first composition in the concentration of from about 0.001% to about 2% by weight based on the total weight of said first composition and said aminoalkyl- or aminohydroxyalkyl-catechol is present in said second composition in the concentration in the range of from about 0.05% to about 2% by weight based on the total weight of said second composition.

12. The process according to claim 11 wherein said second composition also contains an oxidant at a concentration in the range of from about 0.05% to about 3% by weight based on the total weight of said second composition.

13. The process according to claim 11 wherein said aminoalkyl- or aminohydroxyalkyl-catechol is selected from the group consisting of: 3-(3,4-dihydroxyphenylalanine), epinephrine, 3,4-dihydroxyphenylethylamine, 2-hydroxy-(3,4-dihydroxyphenyl)-ethylamine, 3,4-hydroxybenzyl-amine, and mixtures thereof.

14. The process of claim 12 wherein said aminoalkyl- or aminohydroxyalkyl-catechol is selected from the group consisting of: 3-(3,4-dihydroxyphenylalanine), epinephrine, 3,4-dihydroxyphenylethylamine, 2-hydroxy-3,4-dihydroxyphenyl)-ethylamine, 3,4-hydroxybenzyl-amine, and mixtures thereof.

15. The process of claim 10 wherein the metallic moiety in the metal salt is at least one of copper, titanium, zinc, iron, nickel, cobalt, lead, silver and manganese.

16. A process for dyeing human hair comprising the step of contacting said hair with at least one metal salt capable of assisting the conversion of a catechol compound to a melanine-like material and with at least one compound of the formula

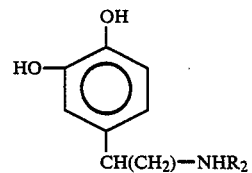

wherein R¹ is H or OH; R² is H or alkyl; and n is 0 or 1.

* * * * *